United States Patent
Arce Vera et al.

(10) Patent No.: US 9,486,425 B2
(45) Date of Patent: Nov. 8, 2016

(54) 4-OXO-2-PENTENOIC ACID AND LIVER DISORDERS

(71) Applicant: NESTEC S.A., Vevey (CH)

(72) Inventors: Francia Jacqueline Arce Vera, Lausanne (CH); Bertrand Bourqui, Murist (CH); Timo Buetler, Zurich (CH); Stephane Duboux, St-Prex (CH); Francis Foata, Lausanne (CH); Philippe Alexandre Guy, Lucens (CH); Nicolas Page, Lausanne (CH); Serge Andre Dominique Rezzi, Semsales (CH)

(73) Assignee: Nestec S.A., Vevey (CH)

( * ) Notice: Subject to any disclaimer, the term of this patent is extended or adjusted under 35 U.S.C. 154(b) by 3 days.

(21) Appl. No.: 14/389,069

(22) PCT Filed: Mar. 25, 2013

(86) PCT No.: PCT/EP2013/056272
§ 371 (c)(1),
(2) Date: Sep. 29, 2014

(87) PCT Pub. No.: WO2013/144085
PCT Pub. Date: Oct. 3, 2013

(65) Prior Publication Data
US 2015/0087706 A1 Mar. 26, 2015

(30) Foreign Application Priority Data
Mar. 30, 2012 (EP) .................................. 121623870

(51) Int. Cl.
*A61K 31/19* (2006.01)
*A23L 1/30* (2006.01)
*A61K 35/74* (2015.01)

(52) U.S. Cl.
CPC .................. *A61K 31/19* (2013.01); *A23L 1/30* (2013.01); *A61K 35/74* (2013.01); *A23V 2002/00* (2013.01); *A23Y 2300/29* (2013.01)

(58) Field of Classification Search
None
See application file for complete search history.

(56) References Cited

FOREIGN PATENT DOCUMENTS

WO    9313076    7/1993

OTHER PUBLICATIONS

Shin SM, Yang JH, Ki SH. Role of the Nrf2-ARE pathway in liver diseases. Oxid Med Cell Longev. 2013;2013:763257. Epub May 9, 2013.*
Kakinuma et al. "Structure-Activity Relationship and Design of an Antimutagen against the UV-Induced Mutation of *Escherichia coli*" Agric. Biol. Chem., vol. 50, 1986, pp. 625-631.
Klassen et al. "Nrf2 the rescue: Effects of the Antioxidative/electrophilic response on the liver" Toxicology and Applied Pharmacology, vol. 244, 2010, pp. 57-65.
Aleksunes, Lauren M. et al. "Emerging Role of Nrf2 in protecting Against Hepatic and Gastrointestinal Disease" Toxicologic Pathology, 35:459-473, 2007.

* cited by examiner

*Primary Examiner* — Anna Pagonakis
(74) *Attorney, Agent, or Firm* — K&L Gates LLP (57) ABSTRACT

The present invention relates generally to compositions with a health benefit. In particular, the invention relates to treatment or prevention of liver disorders. A subject matter of the invention is a composition comprising 4-oxo-2-pentenoic acid for use in the treatment or prevention of liver disorders. A further subject matter of the invention is a composition comprising 4-oxo-2-pentenoic acid for use in the treatment or prevention of liver disorders linked to an insufficient activity of phase II enzymes in the liver.

8 Claims, 8 Drawing Sheets

4-OXO-2-PENTENOIC ACID AND LIVER DISORDERS

CROSS REFERENCE TO RELATED APPLICATIONS

The present application is a National Stage of International Application No. PCT/EP2013/056272, filed on Mar. 25, 2013, which claims priority to European Patent Application No. 12162370.6, filed Mar. 30, 2012, the entire contents of which are being incorporated herein by reference.

The present invention relates generally to compositions with a health benefit. In particular, the invention relates to treatment or prevention of liver disorders. A subject matter of the invention is a composition comprising 4-oxo-2-pentenoic acid for use in the treatment or prevention of liver disorders. A further subject matter of the invention is a composition comprising 4-oxo-2-pentenoic acid for use in the treatment or prevention of disorders linked to an insufficient activity of phase II enzymes in the liver.

The liver is the largest organ within the body. It serves as the body's chemical factory, performing many vital functions—from regulating the levels of chemicals in the body to producing substances that make blood clot. Due to its critical role in so many of the body's processes, disorders linked to liver function are a major cause of ill health. According to the British Liver Trust, liver disease is the fifth "big killer" in England and Wales after heart, cancer, stroke and respiratory disease (http://www.britishlivertrust.org.uk, viewed 1 Nov. 2011). As people can survive with 70% liver damage there is a substantial burden of morbidity from liver disease and a huge economic and human cost from liver-related ill health.

The liver is the main organ responsible for the biotransformation and subsequent detoxification of xenobiotics. Xenobiotics are chemicals which are found in the body but which are not normally produced or expected to be present in it. The term xenobiotics also refers to substances which are present in much higher concentrations than usual. In order to excrete lipophilic xenobiotics in urine they must be made water soluble. The biotransformation of a lipophilic compound to a water-soluble compound in the body normally occurs in two phases: functionalization and then conjugation. Functionalization uses oxygen to form a reactive site and is termed phase I detoxification. Conjugation results in the addition of a water-soluble group to the reactive site and is termed phase II detoxification. There are a number of enzymes which catalyse phase II detoxification, for example heme oxygenase 1, NAD(P)H dehydrogenase quinone 1, glutathione reductase, glutamate cystein ligase, glutathione S-transferase and UDP-glucuronosyltransferase. The activity of these phase II enzymes in the liver is of particular importance due to the liver's major role in detoxification.

Current therapeutic interventions for treating liver disorders are very limited. Where a cause can be identified then removing that cause plays an important role in prevention and/or treatment. For example, when the disorder is due to excessive alcohol consumption or obesity then stopping drinking or making the appropriate lifestyle and diet changes is important. People should similarly be advised to take precautions to avoid infection by viral hepatitis.

Oxidative stress and inflammation play key roles in the pathogenesis of liver diseases and so compounds which target these have been proposed for the treatment or prevention of liver disorders. For example, oltipraz (4-methyl-5-(2-pyrazinyl)-3-dithiolethione) has been shown to protect the livers of mice from α-naphthylisothiocyanate (ANIT)-induced cholestasis as well as decreasing aflatoxin-induced hepatocarcinogenesis in rats. The synthetic triterpenoid 2-Cyano-3,12-dioxoolean-1,9-dien-28-oic acid (CDDO) can lead to hepatoprotection, together with the corresponding methyl (CDDO-Me) and imidazole (CDDO-Im) esters (C. D. Klaassen et al., Toxicology and Applied Pharmacology, 244, 57-65 (2010)). However, these compounds may also produce undesirable effects; for example, clinical trials with oltipraz have shown significant side effects (Y. Zhang et al., Molecular Cancer Therapeutics 3, 885-893 (2004)). It would thus be desirable to have additional compositions available for the treatment or prevention of liver disorders without the drawbacks of those described in the prior art. In particular, it would be highly desirable to find an effective composition whose active ingredient is obtained from a natural source.

Consequently, it was the object of the present invention to improve the state of the art and in particular to provide an alternative composition for use in the treatment or prevention of liver disorders. The inventors were surprised to see that the object of the present invention could be achieved by the subject matter of the independent claim. The dependent claims further develop the idea of the present invention.

Accordingly, the present invention provides a composition comprising 4-oxo-2-pentenoic acid for use in the treatment or prevention of liver disorders.

The present invention also provides the use of 4-oxo-2-pentenoic acid in the preparation of a composition for the treatment or prevention of liver disorders.

"Treatment" within the scope of the present invention refers to reduction, inhibition, alleviation or amelioration.

4-oxo-2-pentenoic acid has the CAS number 4743-82-2 and the following formula

The inventors were surprised to find that 4-oxo-2-pentenoic acid activates Nrf2. Nrf2 (nuclear factor (erythroid-derived 2)-like 2) is a master regulator of antioxidant response in cells. The significance of Nrf2 in the liver is well recognised, as livers of Nrf2-null mice are more susceptible to various oxidative/electrophilic stress-induced pathologies than wild-type mice (C. D. Klaassen et al., Toxicology and Applied Pharmacology, 244, 57-65 (2010)). The transcription factor Nrf2 is found in cells in the cytosol and is bound to an inhibitor Keap1. When bound to Keap1, Nrf2 is also rapidly degraded by the proteasome hence its low basal concentration. When oxidative stress occurs, Nrf2 is released from Keap1. Nrf2 concentration increases and it translocates into the nucleus. It stimulates the expression of genes encoding detoxifying enzymes and antioxidant proteins, thereby increasing the resistance to oxidative stress and electrophilic agents.

Reactive oxygen species and oxidative stress play an important role in the development of hepatic diseases (Y.-P. Wang et al., World Chinese Journal of Digestology, 18, 1907-1911 (2010)). The activation of Nrf2 in the liver is known to treat or prevent liver disorders. For example, recent reviews by Aleksunes (L. M. Aleksunes et al., Toxicologic Pathology, 35, 459-473 (2007)) and Klaassen (C. D. Klaassen et al., Toxicology and Applied Pharmacology, 244, 57-65 (2010)) have linked Nrf2 activation to the treatment of disorders including cholestatic liver disease, inflammatory liver injury, paracetamol hepatoxicity, aflatoxin-induced carcinomas, chemical-induced carcinogenesis, ethanol-mediated hepatotoxicity, liver fibrosis, hepatocellular apoptosis and heavy metal toxicity as well as preventing high-fat diet-induced increases in body weight, adipose mass and hepatic lipid accumulation.

Activation of Nrf2 can be achieved by pharmacological means. For example oltipraz, CDDO, CDDO-Me and CDDO-Im (discussed above) lead to hepatoprotection via Nrf2 activation (C. D. Klaassen et al., Toxicology and Applied Pharmacology, 244, 57-65 (2010)).

Nrf2 activating compounds present in food have been described. These include curcumin, a major component of turmeric (US2009/0042980); resveratrol, found in grapes (Chen C Y et al., Biochem Biophys Res Commun 2005 Jun. 17; 331(4):993-1000); sulphoraphane, found in broccoli (F. Elbarbry et al., Journal of Medical Plants Research, 5, 473-484, (2011)); quercitin, found in apples (Tanigawa S et al., Free Radic Biol Med 2007 Jun. 1; 42(11):1690-703) genistein, found in soybeans and coffee; kaempferol, found in kale; ellagic acid, found in strawberries and raspberries; and epicatechin flavonoids, found in green tea (B. H. J. Juurlink, Canadian Journal of Pharmacology, 79, 266-282 (2001)). As well as activating Nrf2 they have all been reported to induce phase II enzymes. However, the Nrf2 activating compounds are present in these foods at low levels and so large quantities of the natural source materials would be required to extract a significant quantity of the Nrf2 activating compounds. The very low aqueous solubility of curcumin, resveratrol, sulphoraphane and quercitin affects their bio-availability. Therefore, there remains a need to identify further compounds which activate Nrf2, in particular compounds obtainable from natural sources in significant quantities and compounds with good solubility in water.

Nrf2 is known to mediate the induction of phase II enzymes. The inventors therefore investigated whether 4-oxo-2-pentenoic acid would stimulate the expression of genes coding for phase II enzymes in the liver. The inventors found that 4-oxo-2-pentenoic acid activated gene expression in liver cells (hepatocytes) of the following phase II enzymes: heme oxygenase 1, NAD(P)H dehydrogenase quinone 1, glutathione reductase, glutamate cystein ligase, glutathione S-transferase and UDP-glucuronosyltransferase.

An insufficient activity of phase II enzymes in the liver has been linked to disorders such as environmental sensitivities, drug intolerances, pathological detoxification of the liver, chronic fatigue syndrome and fibromyalgia. A composition comprising 4-oxo-2-pentenoic acid provides a method of treating these disorders.

Inhibition of the transcription factor nuclear factor κB (NF-κB) has been shown to prevent acute and chronic liver injury (P. Muriel, Journal of Applied Toxicology, 29, 91-100 (2009)). NF-κB is a pivotal transcription factor in chronic immune responses and inflammatory diseases (P. J. Barnes et al., The New England Journal of Medicine, 336, 1066-1078 (1997)). NF-κB is activated by numerous stimuli, including cytokines, protein kinase C activators, viruses, immune stimuli and, above all, reactive oxygen species (F. Luft, Current Hypertension Reports, 3, 61-67 (2001)). NF-κB consists of homodimers and heterodimers of Rel proteins. The predominant transactivating form of NF-κB consists of p65 and p50 heterodimers. The activation of NF-κB involves the phosphorylation and subsequent proteolytic degradation of the inhibitory protein IκB by specific IκB kinases. The free NF-κB passes into the nucleus, where it binds to κB sites in the promoter region of numerous genes involved in inflammation.

Inhibitors of NF-κB have been identified, such as glucocorticoids (Adcock et al., American Journal of Physiology—Cell Physiology, 268, C331-C338 (1995)) but glucocorticoids have endocrine and metabolic side effects when given systemically. Heparin has also been reported to inhibit NF-κB (WO200119376), but it has the potential side-effect of causing heparin-induced thrombocytopenia.

The inventors investigated whether 4-oxo-2-pentenoic acid inhibits NF-κB activation. Using human colonic cells and human monocytes/macrophages exposed to pro-inflammatory stresses (LPS and rhTNF-α) they found that 4-oxo-2-pentenoic acid inhibits NF-κB activation.

The inventors were surprised to find that 4-oxo-2-pentenoic acid was obtainable from natural sources, e.g., from some heat treated bacterial strains. For example, bacterial preparations of *Bifidobacterium breve* CNCM I-3865 and *Bifidobacterium breve* ATCC 15700™ both yielded 4-oxo-2-pentenoic acid when heated for 6 hours at 90° C. 4-oxo-2-pentenoic acid was found to be in the soluble fraction after centrifuging and filtering the heat treated bacterial preparations.

*Bifidobacterium breve* CNCM I-3865 was deposited with the COLLECTION NATIONALE DE CULTURES DE MICROORGANISMES (CNCM), INSTITUT PASTEUR, 25 rue du Docteur Roux, F-75724 PARIS Cedex 15, France, on Nov. 15, 2007.

*Bifidobacterium breve* ATCC 15700™ can be obtained commercially, e.g., from the American type Culture Collection (ATCC), Manassas, Va., USA, under the trademark ATCC 15700.

Consequently the present invention relates in part to a composition comprising 4-oxo-2-pentenoic acid for use in the treatment or prevention of liver disorders wherein the composition is not to be used as a pharmaceutical. A pharmaceutical is a drug or medicine that is prepared or dispensed in pharmacies and used in medical treatment (<URL: www.thefreedictionary.com/pharmaceutical/> [retrieved on 17-07-2012]). The present invention may be a food composition comprising 4-oxo-2-pentenoic acid for use in the treatment or prevention of liver disorders. The liver disorders may be selected from the group consisting of hepatitis; liver fibrosis; cholestatic liver disease; inflammatory liver injury; xenobiotic toxicity, including drug-induced hepatoxicity and ethanol-mediated hepatoxicity; hepatic encephalopathy; fatty liver disease; ischemia-reperfusion liver injury; liver failure; hereditary tyrosinemia type 1; hepatocellular carcinomas including those induced by hepatitis, aflatoxin and chemical toxins; environmental sensitivities, drug intolerances, chronic fatigue syndrome and fibromyalgia, attributed to an excessive overload of toxins coming into phase I with an inefficient phase II pathway; pathological detoxification of the liver and combinations thereof. These disorders all have an oxidative stress component and can be treated by Nrf2 activation in the liver, often combined with NF-κB inhibition. For example, a composition comprising 4-oxo-2-pentenoic acid may be used in the treatment or prevention of disorders that are treatable by Nrf2 activation in the liver.

Hepatitis is inflammation of the liver. A group of viruses known as the hepatitis viruses cause most cases of hepatitis worldwide, but it can also be due to toxins, other infections and autoimmune diseases.

Liver fibrosis refers to the accumulation of tough, fibrous scar tissue in the liver and is one consequence of inflammation or direct toxic insult to the liver.

Cholestasis is a condition where bile cannot flow from the liver to the duodenum. It can be acquired as a side effect of many medications. Nrf2 activators have been shown to be useful for the treatment of cholestatic liver disease, not only by decreasing the oxidative stress caused by a build-up of bile acids, but also by mobilizing and excreting toxic bile acids through regulation of the Bsep (Bile salt efflux pump) protein.

Liver cell death can trigger an inflammatory response. Central to this inflammatory response is promotion of reactive oxygen species (ROS) formation. Inflammation is a vital part of the innate immune response to microbial infections and tissue trauma. However, an excessive inflammatory response can lead to inflammatory liver injury.

A number of compounds can prove toxic to the liver and lead to liver disorders. Examples of such hepatoxins include lipopolysaccharides; drugs such as paracetamol (acetaminophen) anabolic steroids, some antibiotics and glucocorticoids; ethanol; bromobenzene; carbon tetrachloride; thioacetamide; furosemide; phalloidin; arsenic; pentachlorophenol (PCB); pyrazole; diethyl maleate; paraquat; colchicine; and excessive amounts of the so called "heavy metals" such as iron, manganese, aluminium, mercury, cadmium, beryllium and arsenic. Hepatic encephalopathy is the occurrence of confusion, altered level of consciousness or coma caused by an accumulation in the bloodstream of toxic substances that are normally removed by the liver.

Fatty liver disease is a condition where large vacuoles of triglyceride fat accumulate in liver cells (hepatic lipid accumulation) via the process of steatosis. Despite having multiple causes, fatty liver can be considered a single disease that occurs worldwide in those with excessive alcohol intake and those who are obese (with or without effects of insulin resistance). Accumulation of fat may also be accompanied by a progressive inflammation of the liver. Depending on the contribution of alcohol, fatty liver may be termed alcoholic or non-alcoholic fatty liver disease (or alcoholic or non-alcoholic steatosis).

Reperfusion injury is the tissue damage caused when blood supply returns to the tissue after a period of ischemia or lack of oxygen. Ischemia-reperfusion liver injury occurs in a number of clinical settings, including liver surgery, transplantation, and hemorrhagic shock with subsequent fluid resuscitation, leading to significant morbidity and mortality. It is characterized by significant oxidative stress accompanied by depletion of endogenous antioxidants.

Hepatocellular carcinoma (also called malignant hepatoma) is the most common type of liver cancer. Most cases of hepatocellular carcinoma are secondary to either a viral infection or cirrhosis. Hepatocellular carcinoma can be caused by exposure to aflatoxins which are ubiquitous contaminates of the human food supply throughout the economically developing world. Aflatoxin exposures multiplicatively increase the risk of liver cancer in people chronically infected with hepatitis B virus. Hepatocellular carcinoma can also be induced by chemical toxins such as herbicides, vinyl chloride and arsenic. Although chemical carcinogenesis is multifactorial, oxidative stress is a key component for cellular transformation.

Liver failure is the inability of the liver to perform its normal synthetic and metabolic function as part of normal physiology.

Type 1 Tyrosinemia, also known as hepatorenal tyrosinemia, is caused by a deficiency of the enzyme fumarylacetoacetate hydrolase.

Pathological detoxification of the liver refers to a condition where the phase I and phase II detoxification pathways are not in balance, with phase I increased relative to phase II. Environmental sensitivities, drug intolerances, chronic fatigue syndrome and fibromyalgia may be attributed to an excessive overload of toxins coming into phase I, with an inefficient phase II pathway. Environmental sensitivities, or multiple chemical sensitivities is a chronic, recurring disease caused by a person's inability to tolerate an environmental chemical or class of foreign chemicals. Chronic fatigue syndrome is a significantly debilitating medical disorder or group of disorders generally defined by persistent fatigue accompanied by other specific symptoms for a minimum of six months, not due to ongoing exertion, not substantially relieved by rest, nor caused by other medical conditions. The disorder may also be referred to as myalgic encephalomyelitis, post-viral fatigue syndrome or chronic fatigue immune dysfunction syndrome. Fibromyalgia is a medical disorder characterized by chronic widespread pain and allodynia, a heightened and painful response to pressure. It is advantageous to provide a composition for use in the treatment or prevention of all the liver disorders described above.

The present invention provides a composition comprising 4-oxo-2-pentenoic acid for use in the treatment or prevention of disorders linked to an insufficient activity of phase II enzymes in the liver. "Insufficient activity of phase II enzymes" within the scope of the present invention includes an activity insufficient to achieve or maintain a normal healthy functioning of the phase II detoxification pathway; an activity insufficient to correctly balance or compensate for a disturbed level of phase I detoxification pathway; and/or an activity insufficient to control, reduce or prevent chronic disease through the processing of xenobiotics including drugs, prodrugs and toxins.

The phase II enzymes may be selected from the group consisting of heme oxygenase 1, NAD(P)H dehydrogenase quinone 1, glutathione reductase, glutamate cystein ligase, glutathione S-transferase, UDP-glucuronosyltransferase, and combinations thereof. It is advantageous to be able to treat or prevent disorders linked to an insufficient activity of these phase II enzymes.

Heme oxygenase or haem oxygenase is an enzyme that catalyzes the degradation of heme. This produces biliverdin, iron, and carbon monoxide. There are three known isoforms of heme oxygenase. Heme oxygenase 1 (HO-1) is an inducible isoform in response to stress such as oxidative stress, hypoxia, heavy metals and cytokines. NAD(P)H dehydrogenase quinone 1 (Nqo1) is a cytosolic flavoprotein. It catalyzes the two electron reductive metabolism and detoxification of endogenous and exogenous chemicals as well as defending against intracellular oxidative stress by scavenging superoxide. Glutathione reductase (Gsr) is an enzyme that reduces glutathione disulphide to glutathione, which is an important cellular antioxidant. Glutamate cysteine ligase (GCL) is the first enzyme in the glutathione biosynthesis pathway. GCL performs the rate-limiting step in glutathione synthesis. GCL is a heterodimeric enzyme composed of two proteins: Glutamate cysteine ligase catalytic subunit (Gcic), which possesses all of the catalytic properties, and glutamate cysteine ligase modifier subunit (Gclm), which increases the catalytic efficiency of Gcic. Enzymes of the glutathione S-transferase (Gst) family are composed of many cytosolic, mitochondrial, and microsomal proteins. Gst enzymes catalyze the conjugation of chemicals and electrophilic species with glutathione. These conjugates are subsequently degraded to mercapturates and excreted from the body. UDP-glucuronosyltransferase (UGT) enzymes catalyze the conjugation of exogenous and endogenous chemicals with glucuronic acid, a major part of the phase II detoxification pathway.

The composition of the present invention may be advantageously administered to subjects with an increased activity of phase I enzymes in the liver and/or a reduced activity of phase II enzymes in the liver. The activities of phase I enzymes and phase II enzymes should normally be in balance, with the phase I enzymes producing reactive intermediates which the phase II enzymes conjugate and remove. An increased activity of phase I enzymes without a corresponding increase in phase II enzymes, or a reduced activity of phase II enzymes upsets this balance and leads to a higher level of reactive intermediates which can cause damage to DNA, RNA and proteins. An increased activity of phase I enzymes can for example be caused by polycyclic hydrocarbons from cigarette smoke and aryl amines from meat grilled at high temperatures. These induce Cyp1A1 and Cyp1A2 enzymes, leading to a substantial increase in phase I activity with little or no induction of phase II enzymes. A common mechanism for the inhibition of phase II enzymes is the depletion of necessary cofactors. In humans, sulphation is particularly susceptible to inhibition due to compromised cofactor status. Sulphate reserves must be maintained through dietary intake of sulphur-containing amino acids or inorganic sulphate. Imbalance between phase I and phase II enzyme activities can be countered by administering compositions which activate the phase II enzyme pathway.

Increased toxic load in the liver may lead to inhibition of detoxification by simply overwhelming the systems and competing for detoxification enzyme activities. If the phase I and II detoxification pathways become overloaded there will be a build up of toxins in the body. Many of these toxins are fat soluble and become incorporated in fatty parts of the body where they may stay for years. The brain and the endocrine glands are fatty organs and are common sites for fat-soluble toxins to accumulate. This may result in symptoms of brain dysfunction and hormonal imbalances. Accordingly it is advantageous that the present invention also provides a composition comprising 4-oxo-2-pentenoic acid to be administered to subjects in need of liver detoxification.

Being overweight or obese are well-known disorders that represent a significant burden in our society today. "Overweight" is defined for an adult human as having a Body Mass Index (BMI) between 25 and 30. "Body mass index" is calculated as the ratio of a human's weight in kg divided by their height in metres, squared.

"Obesity" is a condition in which the natural energy reserve, stored in the fatty tissue of animals, in particular humans and other mammals, is increased to a point where it is associated with certain health conditions or increased mortality. "Obese" is defined for an adult human as having a BMI greater than 30.

Fatty liver disease is emerging as the most important cause of chronic liver disease in relation to the increasing incidence of obesity and type 2 diabetes in the population. Non adipose tissues have limited capacity for triacylglycerol storage and under conditions of overnutrition, excess lipids accumulate, determining high levels of saturated fatty acids that can trigger cell dysfunction and/or cell death, a response known as lipotoxicity. The phenomenon involves an elevation of reactive oxygen species levels. Among other things, this redox imbalance is characterized by significant glutathione depletion (L. A. Videl et al., Trends in Molecular Medicine, 12, 555-558 (2006)). The formation of glutathione is promoted by activation of phase II enzymes, and Nrf2 activators are known to reduce high-fat diet-induced increases in hepatic lipid accumulation (S. Shin et al., European Journal of Pharmacology 620, 138-144 (2009)). Accordingly it is advantageous that the present invention also provides a composition comprising 4-oxo-2-pentenoic acid to be administered to subjects who are overweight and/or suffer from type-2 diabetes.

In the present invention the 4-oxo-2-pentenoic acid may be obtainable, for example obtained, from natural sources. Many people are concerned about the safety of materials industrially synthesised from chemical feedstock, especially when these materials are to be ingested, and prefer materials obtained from natural sources.

Surprisingly, the inventors found that some strains of bacteria provide a natural source of 4-oxo-2-pentenoic acid.

In particular, the inventors have found that 4-oxo-2-pentenoic acid can be obtained from *Bifidobacterium breve* CNCM I-3865 or *Bifidobacterium breve* ATCC15700™ (the type strain for *Bifidobacterium breve*). It is particularly advantageous to use bacteria as a natural source of 4-oxo-2-pentenoic acid as the production of large quantities of 4-oxo-2-pentenoic acid is feasible, for example using bioreactors. Accordingly, in the present invention the 4-oxo-2-pentenoic acid may be obtainable, for example obtained, from *Bifidobacterium breve* CNCM I-3865 or *Bifidobacterium breve* ATCC 15700™.

The bacteria may be heat treated at about 60-180° C., preferably at about 80-160° C., for example at about 110-150° C. in commercial production processes. The inventors found that heat treatment at these temperatures provided a satisfactory yield of 4-oxo-2-pentenoic acid within an acceptable time. Without wishing to be bound by theory it is understood that increasing the temperature of heat treatment increases the rate of formation of 4-oxo-2-pentenoic acid but also increases the rate of its degradation. Accordingly these temperatures give a good balance between the rate of formation of 4-oxo-2-pentenoic acid and its degradation.

Typical compositions comprising 4-oxo-2-pentenoic acid may comprise 4-oxo-2-pentenoic acid in an amount of at least 1 mg/kg of the composition. Generally, it is preferred if the composition comprises 4-oxo-2-pentenoic acid in an amount of at least 10 mg/kg of the composition, for example between 50 mg and 50 g per kg of the composition.

The optimum amount of 4-oxo-2-pentenoic acid to be administered can be easily determined by skilled artisans.

In therapeutic applications, compositions are administered in an amount sufficient to at least partially cure or arrest the symptoms of the disorder and/or its complications. An amount adequate to accomplish this is defined as "a therapeutic effective dose". Amounts effective for this purpose will depend on a number of factors known to those of skill in the art such as the severity of the disorder and the weight and general state of the patient. In prophylactic applications, compositions according to the invention are administered to a patient susceptible to or otherwise at risk of a particular disorder in an amount that is sufficient to at least partially reduce the risk of developing a disorder. Such an amount is defined to be "a prophylactic effective dose". Again, the precise amounts depend on a number of patient specific factors such as the patient's state of health and weight.

4-oxo-2-pentenoic acid may be administered in the framework of the present invention in a therapeutic effective dose and/or in a prophylactic effective dose. The composition may be administered in a daily dose corresponding to between 2 µg and mg of 4-oxo-2-pentenoic acid per kg of body weight, preferably between 20 µg and 2 mg of 4-oxo-2-pentenoic acid per kg of body weight, for example between 40 µg and 1 mg of 4-oxo-2-pentenoic acid per kg of body weight.

Liver disorders can affect animals as well as humans, for example hepatitis is a common liver disease in animals. One of the most common liver disorders in cats is feline hepatic lipidosis, also known as feline fatty liver syndrome. Small toy-breed dogs can also susceptible to hepatic lipidosis. Fatty liver disease is also common in livestock, for example dairy cattle and chickens. In a similar manner to humans, there are many toxins which can damage the liver of animals including drugs such as paracetamol, aspirin, anabolic steroids, chemotherapy drugs, some antibiotics, glucocorticoids, anaesthetics, parasite control drugs, and phenylbutazone. Differences in metabolic mechanisms exist between species leading to particular susceptibility to some liver disorders. For example, because cats lack forms of the phase II enzyme glucuronyl transferase, their ability to conjugate compounds such as morphine and phenols is compromised. Dogs are particularly sensitive to glucocorticoid drugs and will develop typical lesions in the liver after multiple dose therapy.

It is therefore an advantage to provide a composition to be administered to humans, pets or livestock. In the case of companion animals such therapies improve the animal's overall quality of life, improve owner satisfaction and improve the bond between the owner and companion animal. An embodiment of the present invention provides a composition to be administered to humans, pets or livestock.

The nature of the composition is not particularly limited. It may be a composition for oral or enteral administration. The composition may be for example selected from the group consisting of a food composition, a food additive, a nutraceutical, a drink, a nutritional formulation, a tube feeding formulation, a powdered composition to be reconstituted in milk or water, and a pet food composition.

Food compositions according to the present invention are diverse in character, for example: milk, yogurt, cheese, fermented milks, milk-based fermented products, ice-creams, cereal-based products or fermented cereal-based products, milk-based powders, chilled or shelf stable beverages, confectionery, animal feed, in particular for domestic animals.

The food composition may also further comprise a protein source, a carbohydrate source, a lipid source, a mineral source and/or a vitamin source. The presence of proteins, carbohydrates, lipids, minerals and/or vitamins may have several advantages. These compounds generally contribute to the taste and mouthfeel of the final product. They also provide the body with nutrients that it may need urgently when it is affected by liver disorders. They also allow formulating the composition of the present invention as a complete nutritional formula, so that no additional nutrition is needed.

Compounds soluble in water have the advantage of being conveniently administered in a number of ways, including orally as solutions. The composition comprising 4-oxo-2-pentenoic acid may be water-based, for example the composition may comprise 4-oxo-2-pentenoic acid dissolved in water.

Those skilled in the art will understand that they can freely combine all features of the present invention disclosed herein. In particular, features described for different embodiments of the present invention may be combined. Further advantages and features of the present invention are apparent from the following figures and non-limiting examples.

Example 1

Nrf2 Activation by 4-Oxo-2-Pentenoic Acid and Bacterial Fractions

Nrf2 Reporter Assay:

Activation of Nrf2 was measured using an Nrf2 reporter assay. This assay is based on the AREc32 cell line, from CRX biosciences (Dundee, Scotland), a stably transfected MCF7 (breast adenocarcinoma) cell line that contains a luciferase gene construct under the control of the ARE. Luciferase is an enzyme which digests luciferin and produces fluorescence. Anti-oxidative molecules such as Tert-butylhydroquinone (TBHQ) induce luciferase transcription via the activation of Nrf2 that binds to ARE. Luciferase activity is determined using a luciferase kit form Promega (Madison, Wis.). The luciferase activity is proportional to the activation of Nrf2.

Nrf2 Activation by Bacterial Fractions:

Three bacterial strains were used to investigate activation of Nrf2 by microorganisms: *Bifidobacterium breve* CNCM I-3865 (NCC2950), *Bifidobacterium breve* CNCM I-3914 (NCC466) and *Bifidobacterium breve* ATCC 15700™ (NCC2791). *Bifidobacterium breve* CNCM I-3914 was deposited with the COLLECTION NATIONALE DE CULTURES DE MICROORGANISMES (CNCM), INSTITUT PASTEUR, 25 rue du Docteur Roux, F-75724 PARIS Cedex 15, France, on Feb. 5, 2008.

For each strain, 10 ml of MRS agar with 0.05% cystein was inoculated with 20 µl of glycerol stock and incubated overnight at 37° C. in anaerobic condition to form pre-cultures. Further cultures were then made by inoculating 10 ml of MRS with 0.05% cystein with the pre-cultures (final $OD_{600}$ adjusted at 0.1). The cultures were incubated for 16 hours at 37° C. in anaerobic conditions to form the P2 cultures. 200 ml of MRS with 0.05% cystein was inoculated with the P2 cultures (final $OD_{600}$ adjusted at 0.1) and the bottles were incubated for 16 hours at 37° C. in anaerobic conditions.

The $OD_{600}$ was measured, the cultures were centrifuged at 3300 g for 10 min and the bacterial pellets were washed two times with cold 1×PBS (phosphate buffered saline) and normalized to OD 50 with 1×PBS.

Bacterial fractions were obtained in two ways for each bacterial strain; a "crude preparation" and a "pure preparation".

The bacterial "crude preparations" were obtained as follows. 5 ml of the OD 50 bacterial preparations were heated for 6 hours at 90° C. in a heating block (Dri-Block DB-3 heating block from Techne, Staffordshire, United Kingdom). The heated bacterial preparations were centrifuged at 3300 g for 10 min at +4° C. and the supernatants were filtered using 0.22 µm syringe filters and stored at +4° C. until further analyses.

The bacterial "pure preparations" were obtained as follows. 5 ml of the OD 50 bacterial preparations were centrifuged at 3300 g for 10 min at +4° C. and the bacterial pellets were re-suspended with 5 ml of water. The bacterial cells were disrupted using mini bead beat (MBB) apparatus in a cold room (six cycles of 90 sec at maximum speed with 10 min of pause between each cycle). The disrupted cells were centrifuged for 1 h at 3300 g at +4° C. and the pellet was re-suspended with 5 ml of 1×PBS and heated for 6 hours at 90° C. in a heating block. The heated preparations were centrifuged for 10 min at 3300 g at +4° C. The supernatants were filtered using 0.22 µm syringe filters and stored at +4° C. until further analyses.

The live bacteria counts of the "OD 50 suspensions" were determined by plating using a spotting method, and the dry weights determined using a halogen moisture analyzer (Metler-Toledo, Greifensee, Switzerland) with the following settings: drying temperature 160° C. with step-drying activated.

To determine the Nrf2 activation the samples were tested on AREc32 cells (seeded in 96 well plates) using 10 independent dilutions (1/2, 1/4, 1/6, 1/10, 1/15, 1/20, 1/25, 1/30, 1/40 and 1/50) and incubated for 24 hours at 37° C. in a 5% CO2/air incubator. The luciferase activity and the cell viability (ATP measurements) were determined using the Luciferase and Cell Titer-Glo kits from Promega.

For each run the luciferase activities, measured in Relative Light Units (RLU), of all the wells were normalized with the mean of the luciferase activity of the cells only of all the plates. Among all the samples tested the normalization procedure was found not to affect the data and this observation permits the comparison of samples measured in different runs.

For each sample the Nrf2 activation was calculated as follows:

1) the Nrf2 Fold Induction:

$$Nrf2\text{fold induction} = \frac{\text{Normalized luciferase activity of the sample}}{\text{Normalized luciferase activity of the cells}}$$

The Nrf2 fold induction is very useful for screening purposes. However the Nrf2 fold induction is a qualitative measurement only, because this calculation does not take into account the sample dilution.

2) the Luciferase Content Per Sample:

(Luciferase content per sample) =

(Normalized luciferase activity of the sample dilution giving the highest $Nrf2$ fold induction) ×

(Dilution factor giving the highest $Nrf2$ fold induction)

The "luciferase content per sample" also reflects Nrf2 activation but can differentiate two samples activating Nrf2 at similar Nrf2 fold inductions since this calculation takes into account the sample dilution.

The luciferase content per sample allows a semi quantification of the Nrf2 activation by reflecting the amount of the Nrf2 activating molecule.

TABLE A

Normalized luciferase activities and calculation of "luciferase content per sample" for crude preparations (OD 50, heated for 6 hours at 90° C.) of *Bifidobacterium breve* ATCC 15700 ™
*Bifidobacterium breve* ATCC 15700
Normalized luciferase content of the cells = 9583

| | Sample dilution | | | | | | | | | |
|---|---|---|---|---|---|---|---|---|---|---|
| | 1/2 | 1/4 | 1/6 | 1/10 | 1/15 | 1/20 | 1/25 | 1/30 | 1/40 | 1/50 |
| Normalized luciferase | 9.37E5 | 3.11E5 | 8.02E4 | 3.28E4 | 2.15E4 | 1.72E4 | 1.54E4 | 1.52E4 | 1.41E4 | 1.32E4 |

TABLE A-continued

Normalized luciferase activities and calculation of "luciferase content per sample" for crude preparations
(OD 50, heated for 6 hours at 90° C.) of *Bifidobacterium breve* ATCC 15700 ™
*Bifidobacterium breve* ATCC 15700
Normalized luciferase content of the cells = 9583

| | Sample dilution | | | | | | | | | |
|---|---|---|---|---|---|---|---|---|---|---|
| | 1/2 | 1/4 | 1/6 | 1/10 | 1/15 | 1/20 | 1/25 | 1/30 | 1/40 | 1/50 |
| Dilution factor | 2 | 4 | 6 | 10 | 15 | 20 | 25 | 30 | 40 | 50 |
| Nrf2 fold induction | 97.8 | 32.5 | 8.4 | 3.4 | 2.2 | 1.8 | 1.6 | 1.6 | 1.5 | 1.4 |

Luciferase content per sample = 9.37E5 × 2 = 1.87E6
(The scientific notation 9.4E5 is equivalent to $9.4 \times 10^5$)

TABLE B

Normalized luciferase activities and calculation of "luciferase content per sample" for crude preparations
(OD 50, heated for 6 hours at 90° C.) of *Bifidobacterium breve* CNCM I-3865
*Bifidobacterium breve* CNCM I-3865
Normalized luciferase content of the cells = 9583

| | Sample dilution | | | | | | | | | |
|---|---|---|---|---|---|---|---|---|---|---|
| | 1/2 | 1/4 | 1/6 | 1/10 | 1/15 | 1/20 | 1/25 | 1/30 | 1/40 | 1/50 |
| Normalized luciferase | 1.16E3 | 1.46E3 | 2.62E3 | 1.24E4 | 1.05E6 | 5.19E5 | 1.04E6 | 8.30E5 | 3.37E5 | 1.87E5 |
| Dilution factor | 2 | 4 | 6 | 10 | 15 | 20 | 25 | 30 | 40 | 50 |
| Nrf2 fold induction | 0.1 | 0.2 | 0.3 | 1.3 | 10.9 | 54.1 | 108.3 | 93.4 | 35.1 | 19.5 |

Luciferase content per sample = 1.04E+06 × 25 = 2.60E+07

Figure 1:
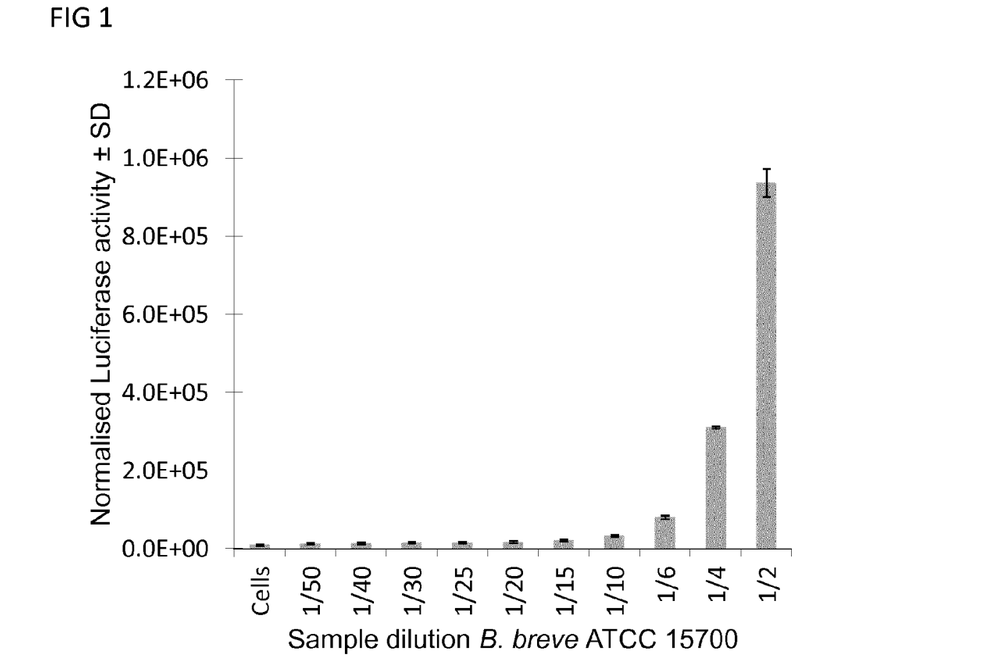
FIG. 1 shows normalized luciferase activities of crude preparations (OD 50, heated for 6 hours at 90° C.) of *Bifidobacterium breve* ATCC 15700™. The results are expressed on the y-axis as a mean±SD of technical triplicates. The x-axis values are the final dilutions of the sample.
Figure 2:
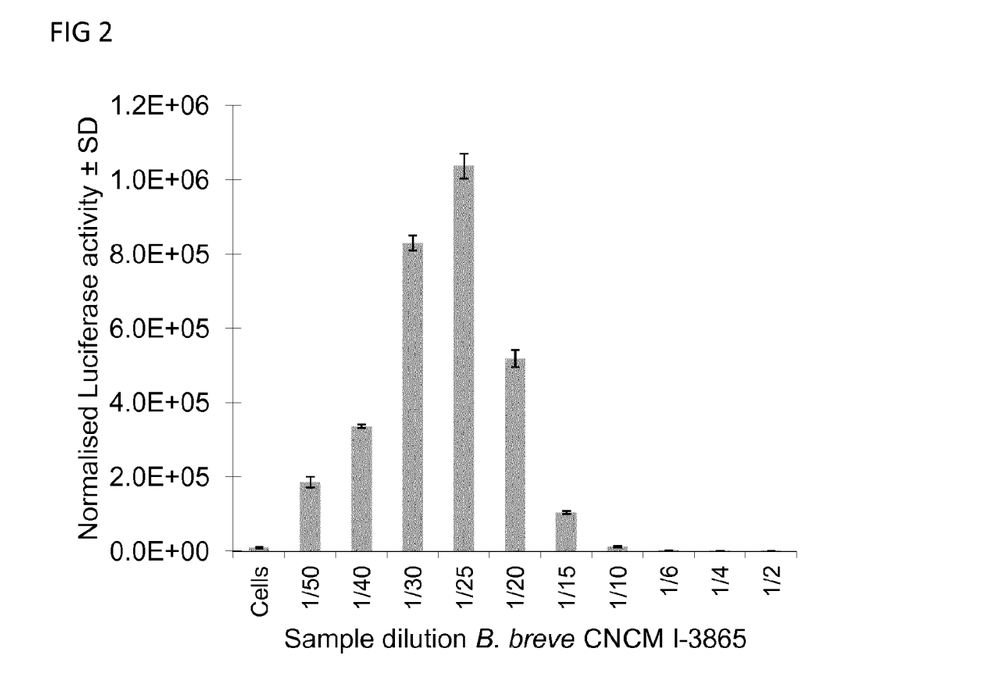
FIG. 2 shows normalized luciferase activities of crude preparations (OD 50, heated for 6 hours at 90° C.) of *Bifidobacterium breve* CNCM I-3865. The results are expressed on the y-axis as a mean±SD of technical triplicates. The x-axis values are the final dilutions of the sample.

As illustrated in tables A and B, both crude preparations of *B. breve* ATCC 15700™ and *B. breve* CNCM I-3865 have similar maximum Nrf2 induction but different luciferase content/sample values. The difference in luciferase content per sample values reflect their corresponding Nrf2 activation patterns (see FIGS. 1 and 2).

In contrast *Bifidobacterium breve* CNCM I-3914 did not significantly activate Nrf2, see comparison table C.

TABLE C

Comparison of results from the three different *Bifidobacterium breve* strains—crude preparation.

| B. breve strain code | cfu/ml | Dry weight (mg/ml) | Normalized luciferase activity | Dilution factor giving the highest Nrf2 fold induction | Nrf2 fold induction | Luciferase content per sample |
|---|---|---|---|---|---|---|
| CNCM I-3865 | 2.5E10 | 24.8 | 1.04E6 | 25 | 108.3 | 2.60E7 |
| ATCC 15700 | 1.7E10 | 23.2 | 9.37E5 | 2 | 97.8 | 1.87E6 |
| CNCM I-3914 | 1.8E10 | 24.1 | 3.06E4 | 2 | 3.2 | 6.12E4 |

TABLE D

Comparison of results from the three different *Bifidobacterium breve* strains—pure preparation.

| B. breve strain code | cfu/ml | Dry weight (mg/ml) | Normalized luciferase activity | Dilution factor giving the highest Nrf2 fold induction | Nrf2 fold induction | Luciferase content per sample |
|---|---|---|---|---|---|---|
| CNCM I-3865 | 2.5E10 | 24.8 | 8.00E5 | 40 | 106 | 3.20E7 |
| ATCC 15700 | 1.7E10 | 23.2 | 6.55E5 | 6 | 68.4 | 3.93E6 |
| CNCM I-3914 | 1.8E10 | 24.1 | 2.42E4 | 2 | 2.5 | 4.84E4 |

Nrf2 Activation by 4-Oxo-2-Pentenoic Acid 4-oxo-2-pentenoic acid (Alfa Aesar—reference L02185) was tested in the Nrf2 reporter assay. Different doses of 4-oxo-2-pentenoic acid were applied on AREc32 cells for 24 h and then the luciferase activity was quantified as described above. The cell viability was also measured using a cell Titer-Glo kit (ATP quantification).

Figure 3:
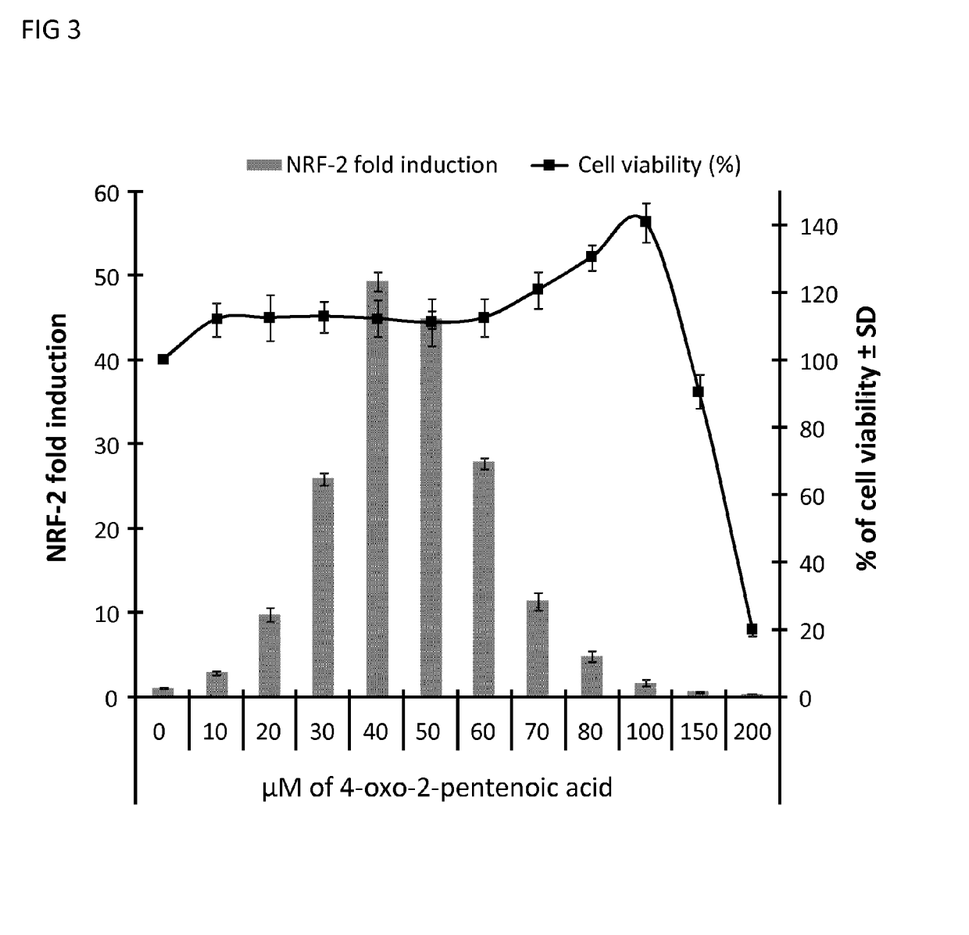
FIG. 3 shows Nrf2 induction-fold (bars) and percentage of cell viability (lines) of AREc32 cells incubated with of a dose range of 4-oxo-2-pentenoic acid from 0 to 200 µM. The Nrf2 fold inductions are ratios between the luciferase activity (RLU) of the AREc32 cells in the presence of 4-oxo-2-pentenoic acid and the basal luciferase activity of the unexposed cells. The cell viability, measured by ATP quantification, is expressed as relative percentages of control (untreated) cells. The results are expressed as means of technical triplicates±SD and are representative of four independent experiments.
Figure 4:
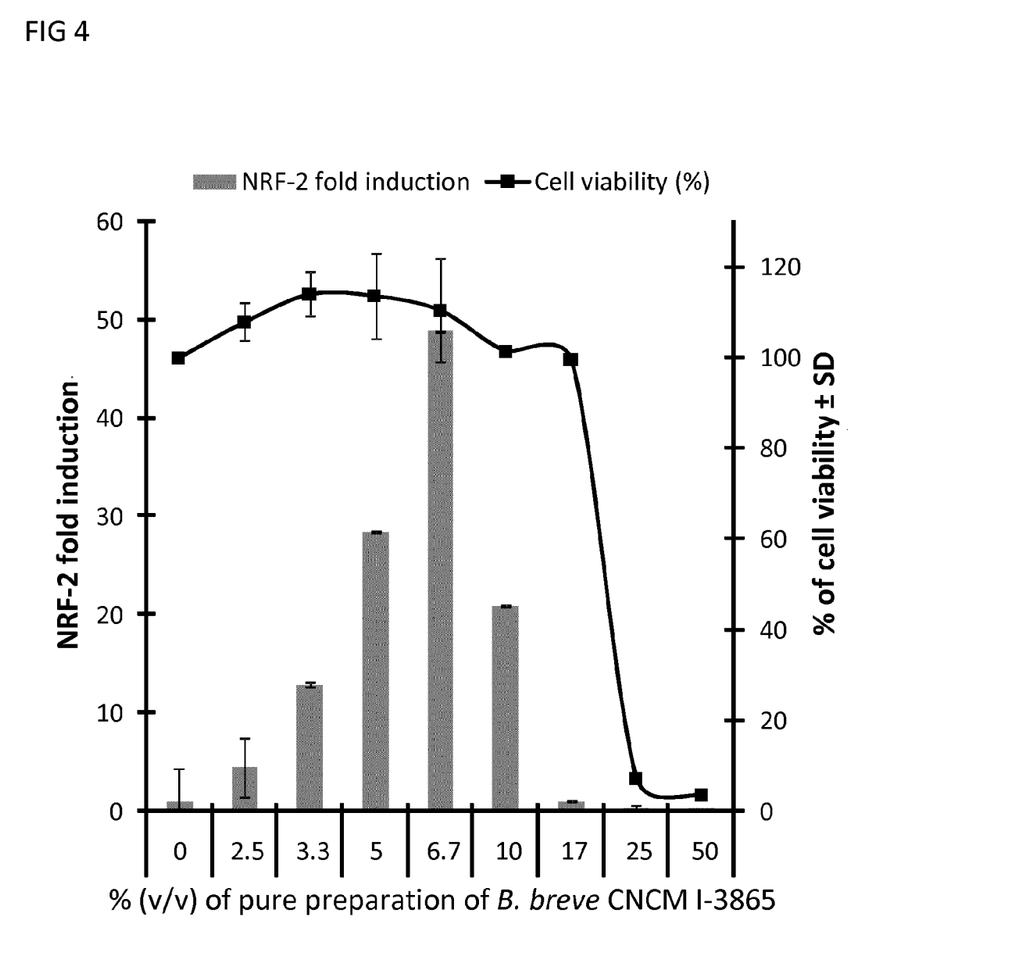
FIG. 4 shows Nrf2 induction-fold (bars) and percentage of cell viability (lines) of AREc32 cells incubated with of a dose range of a "pure preparation" of *Bifidobacterium breve* CNCM I-3865 from 2.5 to 50% v/v. Other details as for FIG. 3.

As shown in FIG. 3, the 4-oxo-2-pentenoic acid molecule was found to strongly activate Nrf2 in a dose dependent manner. The viability of AREc32 cells was not affected by 4-oxo-2-pentenoic acid at doses lower than 70 µM. The optimal dose of Nrf2 activation was around 40-50 µM. For comparison, FIG. 4 shows that a bacterial fraction of *Bifidobacterium breve* CNCM I-3865 activates Nrf2 in a similar manner.

Example 2

Stimulating the Expression of Genes Coding for Phase II Enzymes in the Liver

Hepatocytes were isolated from Sprague-Dawley male rats (190-240 g) by liver perfusion. Cells were seeded at 2500000 cells/dish (6 cm) in 2.5 ml of Williams'E medium supplemented with 2 mM L-glutamine, 10 mM Hepes (Sigma), 1% ITS+, 1% Penicillin/Streptomycin (Sigma) and 25 nM Dexamethasone (Sigma). After overnight incubation, the medium was removed and 2.5 ml of fresh medium containing the test substances was added. The dishes were incubated for 24 h at 37° C. in a 5% $CO_2$/air incubator.

At the end of the incubation, the cell supernatants were harvested for LDH (lactate dehydrogenase) measurement, which is an indicator of cell viability. Cells were washed once with 2.5 ml of cold PBS 1× then detached from the Petri dishes by scraping. Cells were then transferred to 1.5 ml Eppendorf tubes which were centrifuged for 1 min at 4° C. at 7000 g.

Cell lysates for the RNA extraction were obtained by adding 400 µl of RNA lysis buffer (RA-1 with 1% v/v β-mercaptoethanol) to the cells and vigorously mixed (vortex). Total RNA was extracted from the cell lysates according manufacturer's instructions (Nucleospin RNA2 kit, Macherey-Nagel, Düren, Germany) with minor changes: 20 min of DNASE treatment and 60 µl of elution volume.

Total RNAs were quantified using Ribogren kit (Molecular probes) and the quality was evaluated by capillary electrophoresis using Bionalyzer (Agilent).

Reverse transcription reactions were performed with the Multiscribe reverse transcriptase enzyme in the presence of random hexamers primers (Reverse Transcription Reagent from Applied Biosystems). Gene expression quantification was performed using pre-designed TaqMan probes (Applied Biosystems). Each qPCR reaction was done in technical duplicates on 50 ng of cDNA. The arithmetic mean of two housekeeping genes (GAPDH and β-Actin) was used for normalization.

The mRNA gene expression calculations are based on the ΔΔCt method:

Normalized mRNA expression=$2^{-\Delta C_t} \times F$

ΔCt=Ct(goi)−average CT(hk)

F=1000000 (fixed factor used to obtain reasonable numbers)
goi=gene of interest
hk=housekeeping gene

TABLE F

TaqMan probes for genes under the control of Nrf2.

| TaqMan ID | Gene name | Gene alias |
|---|---|---|
| Rn99999916_s1 | GAPDH | GAPDH |
| Rn00667869-m1 | β-ACTIN | Actb |
| Rn00563101-m1 | Glutamate cysteine ligase, catalytic subunit | Gclc |
| Rn00588153_m1 | Glutathione reductase | Gsr |
| Rn00561387_m1 | Heme oxygenase 1 | HO-1 |
| Rn00566528_m1 | NAD(P)H dehydrogenase quinone | Nqo1 |
| Rn00564188_m1 | Glutathione synthetase | Gss |
| Rn00821792_g1 | Glutathione-S-transferase, pi 1 | Gstp1 |
| Rn00821927_g1 | UDP-glucuronosyltransferase (UGT) | LOC286989 |
| Rn00577994_g1 | Glutathione peroxidase 1 | Gpx1 |
| Rn00822100_gH | Glutathione peroxidase 2 | Gpx2 |

Figure 5:
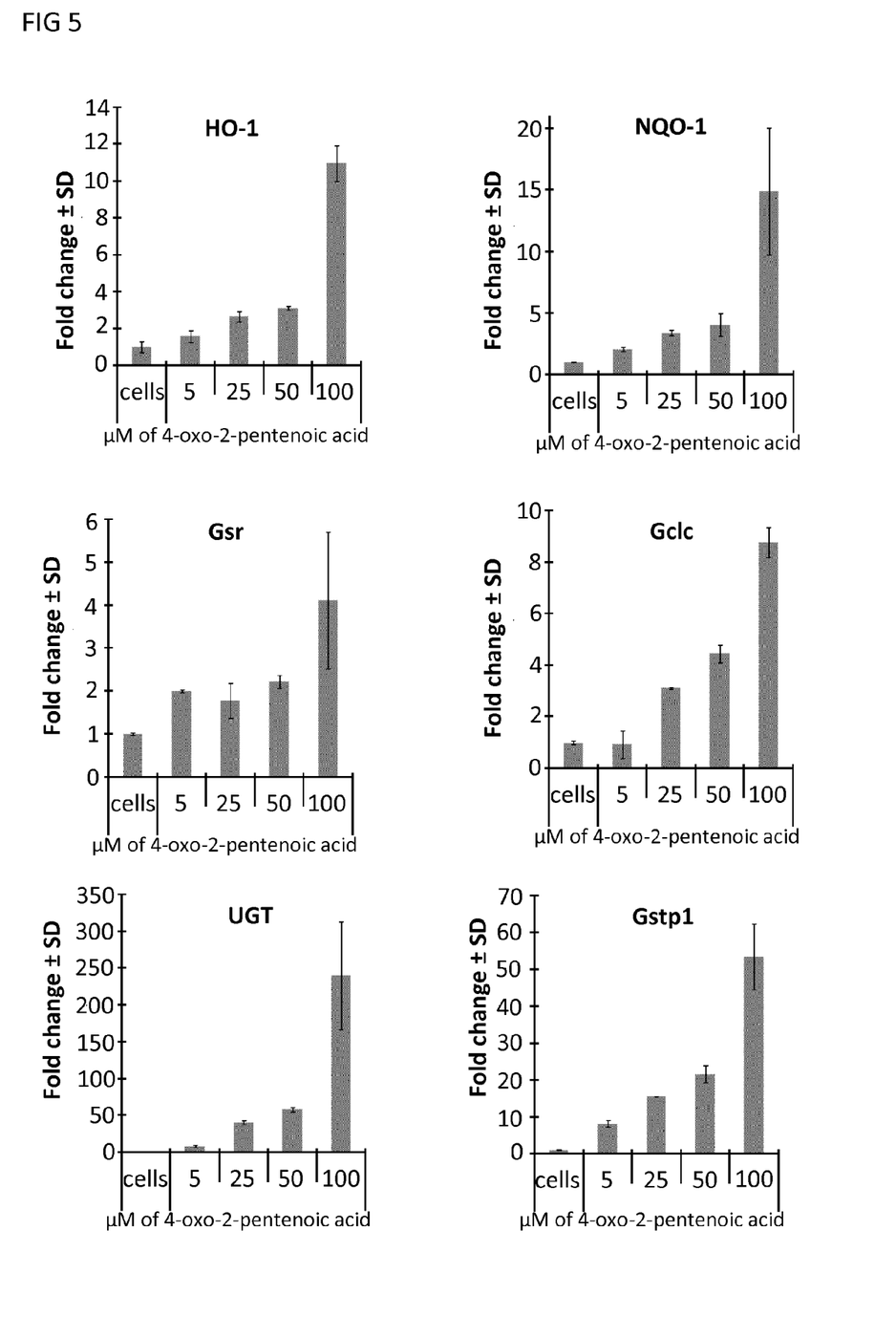
FIG. 5 shows the mRNA expression profiles of genes for phase II enzymes in hepatocytes incubated with a dose range of 4-oxo-2-pentenoic acid for 24 h. The results are representative of two experiment performed in technical duplicates and are expressed as means±SD.

As can be seen in FIG. 5, 4-oxo-2-pentenoic acid increased phase II enzyme genes in the liver: heme oxygenase 1, NAD(P)H dehydrogenase quinone, gluthatione synthetase, glutamate cysteine ligase catalytic subunit, glutathione-S-transferase and UDP-glucuronosyltransferase (UGT). The levels of expression of glutathione peroxidase 1, glutathione peroxidase 2 and glutathione synthetase were not affected by the presence of 4-oxo-2-pentenoic acid. LDH measurements showed that the cell viability was not affected.

Consequently, the presented data allows us to conclude that 4-oxo-2-pentenoic acid can be used for the treatment or prevention of disorders linked to an insufficient activity of phase II enzymes in the liver.

Example 3

Inhibition NF-κB Activation by 4-Oxo-2-Pentenoic Acid (Anti-Inflammatory Effect)

The inventors evaluated the capability of 4-oxo-2-pentenoic acid to inhibit NF-κB activation under pro-inflammatory stresses (LPS and rhINF-α). Two in-vitro systems were used: human colonic cells (HT-29 clone 34) and human monocytes/macrophages (THP-1 blue cells).

HT-29 clone 34

The human colonic adenocarcinoma HT-29 clone 34 cell line (passage 42-50) are adherent cells stably transfected with a NF-κB/SEAP reporter plasmid. They were cultured in DMEM high glucose (4.5 g/L) (Invitrogen) containing 1% of stable L-glutamine and supplemented with 10% of heat inactivated (one hour at 56° C.) Foetal Calf Serum (FCS) (Bioconcept, Allschwil, Switzerland), 1% of Penicillin/Streptomycin (Sigma) and 500 µg/ml of Geneticin (PAA, Pasching, Austria) at 37° C. in a 5% $CO_2$/air incubator. Culture medium was renewed every two days until the cell monolayer reached ~90% confluence. Cells were sub-cultured using 1× Trypsin/EDTA (Sigma).

10000 cells/well were seeded in 200 µl of culture medium in flat bottom white border 96 well plates (Greiner Bio One, Kremsmuenster, Austria). After 3-4 days of culture (i.e. cells reaching ~70-80% confluence), culture medium was removed and 180 µl of experimental medium (DMEM high glucose supplemented with 50 mM of HEPES and 5% of human milk, as a source of sCD14 and LPS Binding Protein (LBP), for LPS stimulation only) containing (or not) dose ranges of 4-oxo-2-pentenoic acid (3 to 400 µM) were added to the cells and the plates were pre-incubated for 4 hours at 37° C. in a 5% $CO_2$/air incubator. 20 µl of experimental medium containing (or not) LPS 055:B5 or rhTNF-α (100 and 10 ng/ml final, respectively) was added and the plates were incubated for 24 hours at 37° C. in a 5% $CO_2$/air incubator.

Cell culture supernatants were then collected for measurement of NF-κB activity (determination of secreted alkaline phosphatase and IL-8 production) using Phosphalight (Applied Biosystems) and IL-8 singleplex (Meso Scale, Gaithersburg, Md.) kits, respectively.

Cell viability was determined by measuring ATP using Cell Titer-Glo kit (Promega). Briefly, remaining adherent HT-29 clone 34 cells were incubated for 10 min at room temperature under horizontal shaking (250 rpm) with 120 µl of Cell Titer-Glo reagent (pre-diluted twice in 1×PBS) and the luminescence was measured using Polarstar microplate reader (BMG, Offenburg, Germany) for 1000 ms with a gain value set to 3500.

In the absence of LPS, no NF-κB activity was observed (based on SEAP or IL-8 detection) in cell culture supernatants of HT-29 clone 34 cells incubated with 4-oxo-2-pentenoic acid at the doses tested.

Figure 6:
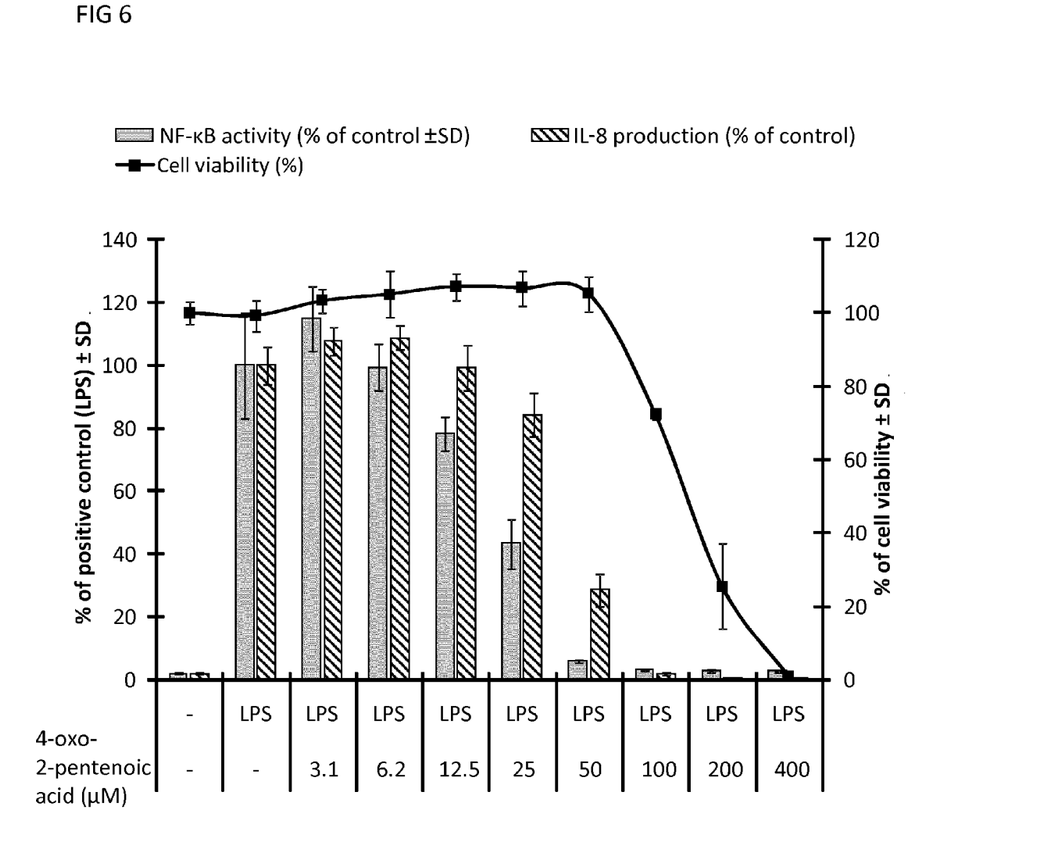
FIG. 6 shows NF-κB activity estimated by the production of SEAP (solid bars) and IL-8 (striped bars) measured in supernatant of HT-29 clone 34 cells stimulated with LPS. The cell viability is shown with a line. The cells were exposed to a dose range of 4-oxo-2-pentenoic acid. Results are expressed as means±SD of two independent experiments performed in technical triplicates.

Measurements of the cell viability of the HT-29 clone 34 cells showed a decrease in cell viability at doses of 4-oxo-2-pentenoic acid higher than ~50 µM (FIG. 6).

When inflammation response is trigged by LPS, 4-oxo-2-pentenoic acid inhibits NF-κB activity in a dose dependent manner (FIG. 6). 4-oxo-2-pentenoic acid impacted on both SEAP and IL-8 secretion, the best inhibition being with 50 µM 4-oxo-2-pentenoic acid). Similar results, although less pronounced, were observed with cells stimulated with rhINF-α.

THP-1 Blue

Human monocytes/macrophages THP-1 blue cells (passage 16-20) (Invivogen, Toulouse, France) were cultured in modified RPMI medium (ATCC, Manassas, Va.) containing 1 mM of sodium pyruvate, 2 mM of L-glutamine, 4.5 g/L of glucose and 10 mM of HEPES supplemented with 10% of heat inactivated FCS (Bioconcept), 1% of Penicillin/Streptomycin (Sigma) and 500 µg/ml of Zeocin (Invivogen) at 37° C. in a 5% $CO_2$/air incubator.

200000 cells/well were seeded in 100 µl of culture medium in 96 well flat bottom transparent plates. After 24 hours of incubation at 37° C. in a 5% $CO_2$/air incubator, 80 µl of culture medium containing (or not) dose ranges of 4-oxo-2-pentenoic acid (5 to 200 µM) were added to the cells and pre-incubated for 5 hours at 37° C. 20 µl of culture media containing (or not) LPS 055:B5 (Sigma) (100 ng/ml final) was added and the plates were incubated for 16 hours at 37° C. in a 5% $CO_2$/air incubator.

Cell culture supernatants were carefully transferred to 96 well-plates for NF-κB activity measurement which is proportional to the level of secreted alkaline phosphatase. Briefly, 100 µl of supernatants were mixed with 150 µl of QuantiBlue (Invivogen) in a 96 well-plates incubated for 3 h at 37° C. before OD measurements at 620 nm with Sunrise microplate reader (Tecan, Mannedorf, Switzerland). Cell viability was determined using Cell Titer-Glo kit as described above.

Figure 7:
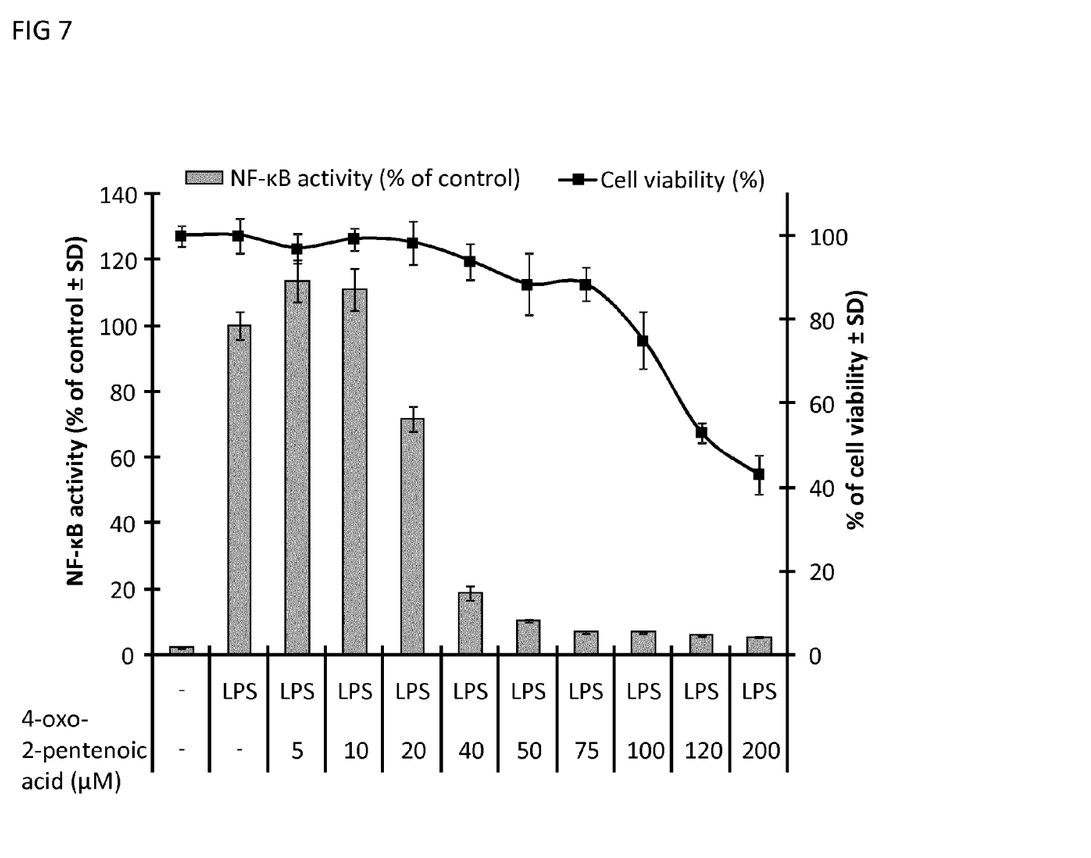
FIG. 7 shows NF-κB activity (bars) and cell viability (lines) of LPS stimulated (0.5 µg/ml) THP-1 blue cells in a presence of a dose range of 4-oxo-2-pentenoic acid for 24 h. Results are expressed as means±SD of two independent experiments performed in technical triplicates.

When stimulated with LPS, strong NF-κB inhibition was obtained in response to 4-oxo-2-pentenoic acid at doses around 40 to 75 µM. 4-oxo-2-pentenoic acid was toxic to cells at doses higher than 75 µM (FIG. 7).

The data generated with HT-29 clone 34 cells and THP-1 blue cells indicate that 4-oxo-2-pentenoic acid inhibits NF-κB activation under pro-inflammatory stresses.

Example 4

Quantification of 4-Oxo-2-Pentenoic Acid by HPLC-MS/MS

In order to quantify 4-oxo-2-pentenoic acid, a high throughput analytical method involving coupling high performance liquid chromatography with electrospray ionization tandem mass spectrometry (HPLC-ESI-MS/MS) was developed.

Methodology:

4-oxo-2-pentenoic acid standard was purchased from Alfa Aesar (Ward Hill, USA). HPLC grade water, methanol and acetic acid were purchased from Lichrosolv (Merck, Darmstadt, Germany). HPLC vials and 2 mm inserts were purchased from Agilent (Santa Clara, Calif.). 4-oxo-2-pentenoic acid was found to be soluble in water to at least 20 mg/ml. 4-oxo-2-pentenoic acid standard compound was solubilised in water at a final stock solution of 10 mg/ml and further diluted in water to build a calibration curve.

HPLC-ESI-MS/MS analyses were carried out on a turbulent flow chromatography (TFC) system (Thermo Fisher, Waltham, Mass.) coupled to a 3200 Q TRAP mass spectrometer (Applied Biosystems). The analytical column used was a Hypersil Gold AQ (3×50 mm, 5 µm) purchased from Thermo Fisher (Waltham, Mass.) running at room temperature and a constant flow rate of 600 µl/min. The mobile phases were constituted with solvent A—water containing 0.05% acetic acid and B—methanol containing 0.05% acetic acid. The gradient program was: 0 min 0% B, held for 40 sec (0-0.67 min) at 0% B, ramping to 50% B in 180 sec (0.67-3.67 min), ramping from 50 to 90% B in 10 sec (3.67-3.83 min), held for 120 sec (5.83 min) at 90% B, before going back to 0% B and held for an additional 300 sec (5.83-10.83 min). The injection volume was 5 µl.

MS data acquisition was realized in electrospray negative ionization mode. MS tuning was performed by infusing a solution of 4-oxo-2-pentenoic acid standard (5 µg/ml in water) at a flow rate of 10 µl/min mixed with a HPLC flow made of solvents A and B (80/20, v:v; 0.6 ml/min) using a T-connector. Nitrogen was used for the nebulizer and curtain gases. The interface heater was activated and the block source temperature was maintained at 700° C. with a capillary voltage set at −4.5 kV. Nitrogen was also used as collision gas at a medium pressure selection. MS/MS detection was realized using the selected reaction monitoring (SRM) acquisition mode. The two most intense fragment ions were selected by scanning m/z 113→69 (collision energy of 11 eV), and m/z 113→41 (collision energy of 26 eV), using a constant dwell times of 50 ms (total scan time of 110 ms). The declustering potential was set at −29 V. Quantitative analyses were performed using the most intense SRM signal whereas the second transition was used for analyte confirmation based on appropriate area ratio calculated from standard solutions. Data processing was performed using Analyst 1.5.1 software (Applied Biosystems).

Figure 8:
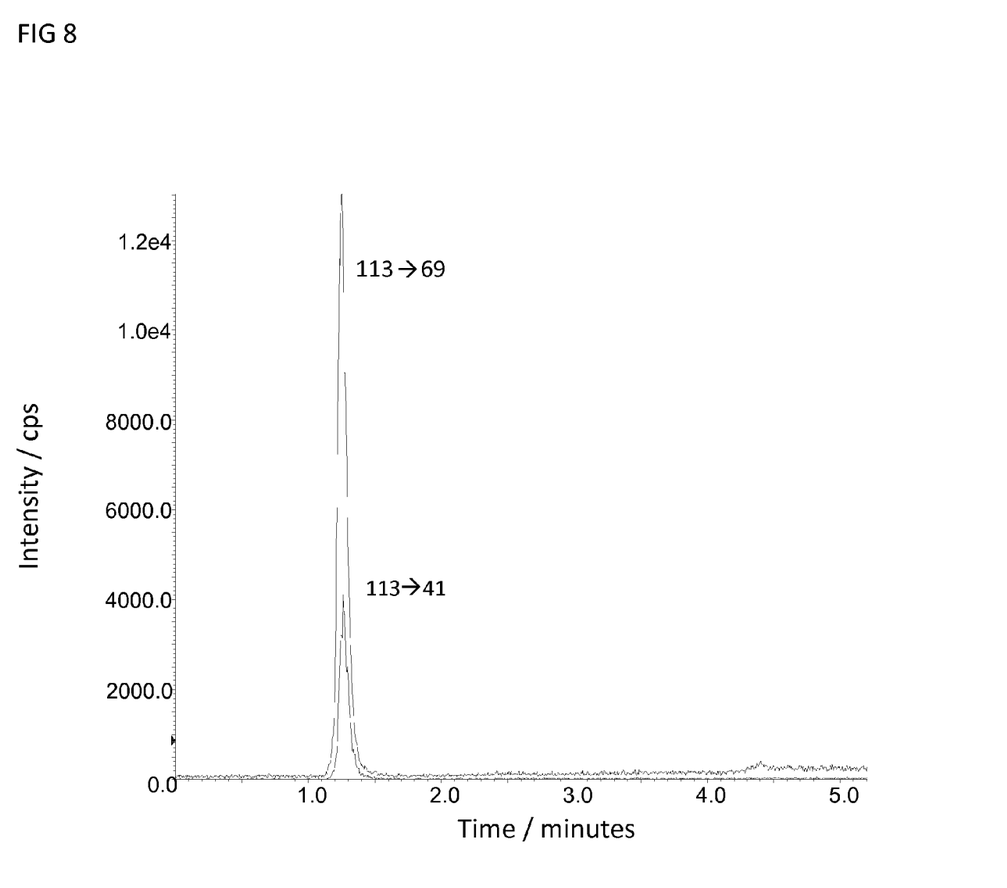
FIG. 8 shows a typical chromatogram of a 4-oxo-2-pentenoic acid standard dissolved in water. The higher SRM is associated to the transition reaction of m/z 113→69, while the lower SRM corresponds to transition reaction of m/z 113→41. The retention time is expressed in minutes (x-axis). Signal intensity (y-axis) is expressed in Cps.

Detection of 4-Oxo-2-Pentenoic Acid in PBS and Water by HPLC-MS/MS:

4-oxo-2-pentenoic acid was solubilised in 1×PBS or water, and the detection by HPLC-MS/MS performed as described in the previous section. The SRM associated to the transition reaction of m/z 113→69 revealed a more intense signal as compared with the SRM associated with the transition m/z 113→41 at a retention time of 1.25 min. Similar retention times for both transitions were observed confirming the validity of the analysis, (FIG. 8). The molecule 4-oxo-2-pentenoic acid was successfully detected in both 1×PBS (data not shown) and water (FIG. 8).

Establishment of 4-Oxo-2-Pentenoic Acid Standard Curve:

In order to quantify precisely the amount of 4-oxo-2-pentenoic acid in bacterial fractions, standard curves were established for 4-oxo-2-pentenoic acid in simple matrices like 1×PBS or HPLC grade water. Commercial 4-oxo-2-pentenoic acid was suspended in 1×PBS and water at different doses. The HPLC-ESI-MS/MS method was then used to quantify the estimated doses of 4-oxo-2-pentenoic acid. Good linearity was observed between the quantity of 4-oxo-2-pentenoic acid (from 0.1 to 25 µg/ml) and the resulting intensities (expressed in cps) both in 1×PBS and HPLC grade water.

Quantification of 4-Oxo-2-Pentenoic Acid in Bacterial Fractions:

4-oxo-2-pentenoic acid was quantified in the heat treated bacterial preparations from example 1. All samples were diluted in HPLC grade water (3 dilutions/sample) before HPLC-ESI-MS/MS analysis. The results are summarized in table E.

TABLE E

Concentrations of 4-oxo-2-pentenoic acid (µg/ml) in crude and pure bacterial heated preparations (OD 50) from example 1 (6 hours of heating at 90° C.). N.D stands for "Not Detectable", below the detection limit of the method.

| Strain | Strain Code | 4-oxo-2-pentenoic acid (µg/ml) Crude preparation | 4-oxo-2-pentenoic acid (µg/ml) Pure preparation |
|---|---|---|---|
| B. breve | CNCM I-3865 | 95.3 | 126.8 |
| B. breve | ATCC 15700 | 2.1 | 16.4 |
| B. breve | CNCM I-3914 | N.D. | N.D. |

Example 5

The Influence of Heating Temperature and Time on the Production of 4-Oxo-2-Pentenoic Acid from *Bifidobacterium breve* CNCM I-3865

To characterize the production of 4-oxo-2-pentenoic acid from *Bifidobacterium breve* CNCM I-3865 upon heat treatment a kinetic experiment was performed using various temperatures. The "master stock" of biomass used for this experiment was produced in bioreactors at 37° C. with MRS medium under anaerobic and pH control conditions. After the grow culture (16 h), the culture media was removed and the cells were washed two times with 1×PBS, concentrated to OD 134 (1.5E+10 cfu/ml) in 1×PBS with 10% glycerol then stored at −80° C. in 50 ml aliquots.

A "working biomass" of *Bifidobacterium breve* CNCM I-3865 was then prepared from the biomass master stock as follows: The biomass was washed two times with 1×PBS and adjusted to OD 40 in 1×PBS.

Figure 9:
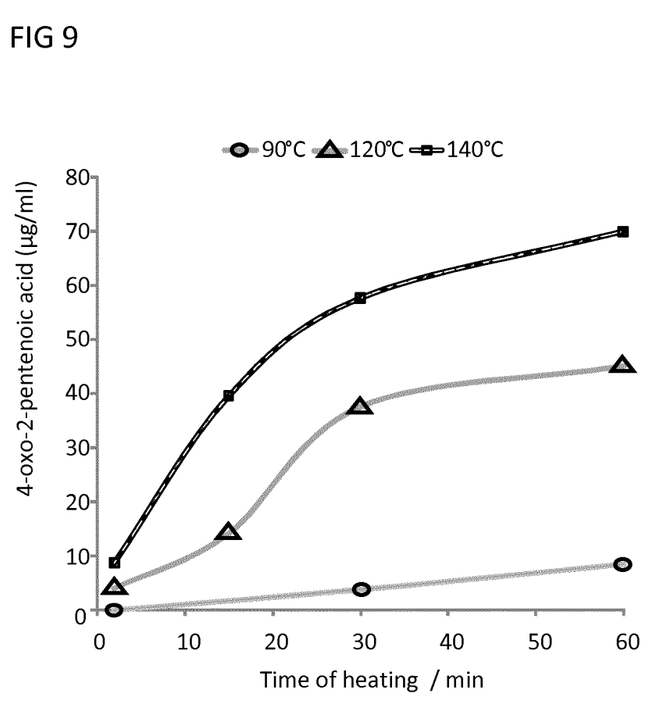
FIG. 9 shows 4-oxo-2-pentenoic acid quantification using HPLC-ESI-MS/MS of crude preparations of *Bifidobacterium breve* CNCM I-3865 (OD 40) heated for 2, 15, 30, and 60 minutes at 90° C. (indicated by circles ○), 120° C. (indicated by triangles Δ) and 140° C. (indicated by squares □).

A Temperature Heating Apparatus (THA) was used to investigate the effect of different heating times and temperatures. This system is a small scale version of typical apparatus found in production environments. Steam is used to heat up a holding tube containing cartridges of biomass. Sample temperatures of 90° C., 120° C. and 140° C. were applied for periods up to 60 minutes. 5 ml of each heat-treated biomass was then centrifuged for 10 min at 5000 g and the supernatants were filtered (0.2 µm) and the 4-oxo-2-pentenoic acid content quantified by HPLC-ESI-MS/MS. The amounts of 4-oxo-2-pentenoic acid generated are shown in FIG. 9.

The invention claimed is:

1. A method for the treatment of a liver disorder comprising administering to a subject in need thereof a non-pharmaceutical composition comprising 4-oxo-2-pentenoic acid, the liver disorder is selected from the group consisting of hepatitis, liver fibrosis, cholestatic liver disease, inflammatory liver injury, drug-induced hepatotoxicity, ethanol-mediated hepatotoxicity, hepatic encephalopathy, fatty liver disease, ischemia-reperfusion livery injury, liver failure, hereditary tyrosinemia type I and hepatocellular carcinoma.

2. The method of claim 1, wherein the 4-oxo-2-pentenoic acid is obtained from *Bifidobacterium breve* CNCM I-3865 or *Bifidobacterium breve* ATCC 15700.

3. The method of claim 2, wherein the *Bifidobacterium breve* CNCM I-3865 or *Bifidobacterium breve* ATCC 15700 was heat treated at about 60-180° C.

4. The method of claim 1, wherein the composition comprises 4-oxo-2-pentenoic acid in an amount of at least 1 mg per kg of the composition.

5. The method of claim 1, wherein the composition is administered to the subject in a daily dose corresponding to between 2 µg and 20 mg of 4-oxo-2-pentenoic acid per kg of body weight.

6. The method of claim 1, wherein the composition is administered to the subject orally or enterally.

7. The method of claim 1, wherein the subject is selected from the group consisting of humans, pets and livestock.

8. The method of claim 1, wherein the composition is selected from the group consisting of a food composition, a food additive, a nutraceutical, a drink, a nutritional formulation, a tube feeding formulation, a powdered composition to be reconstituted in milk or water, and a pet food composition.

* * * * *